United States Patent [19]

Slomski et al.

[11] Patent Number: 5,445,292
[45] Date of Patent: Aug. 29, 1995

[54] SEALABLE THERMOFORMED CONTAINER FOR LIQUIDS

[75] Inventors: Douglas B. Slomski, Batavia; Todd O. Buck, Elburn, both of Ill.

[73] Assignee: Plastofilm Industries, Inc., Wheaton, Ill.

[21] Appl. No.: 118,926

[22] Filed: Sep. 9, 1993

[51] Int. Cl.[6] ............................................. B65D 41/16
[52] U.S. Cl. ............................... 220/306; 220/256; 220/339; 220/738; 4/144.1; 4/144.2
[58] Field of Search ................. 220/23.83, 212, 256, 220/306, 703, 729, 731, 738, 339; 206/546, 570; 4/144.1, 144.2

[56] References Cited

U.S. PATENT DOCUMENTS

| | | | |
|---|---|---|---|
| 995,415 | 6/1911 | Steel | 220/731 |
| 2,776,691 | 1/1957 | Tupper | 220/256 |
| 2,873,052 | 2/1959 | Atherton | 220/731 |
| 3,320,993 | 5/1967 | Motsenbocker | 220/306 |
| 3,452,896 | 7/1969 | Elliot | 220/306 |
| 3,643,266 | 2/1972 | Black | 4/144.2 |
| 3,711,871 | 1/1973 | Sherin | 4/144.1 |
| 3,777,739 | 12/1973 | Raitto | 4/144.1 |
| 3,811,136 | 5/1974 | Whitney et al. | 4/144.1 |
| 3,832,738 | 9/1974 | Kliemann | 220/306 |
| 3,878,571 | 4/1975 | Seeley | 4/144.1 |
| 3,881,465 | 5/1975 | Raitto | 4/144.1 |
| 3,899,107 | 4/1975 | Gaal | 220/731 |
| 3,964,635 | 6/1976 | Ludder | 220/306 |
| 4,042,143 | 8/1977 | Biggins | 220/306 |
| 4,061,226 | 12/1977 | Essen | 220/339 |
| 4,064,760 | 12/1977 | Benjamin | 4/144.1 |
| 4,079,857 | 3/1978 | Crisci | 220/306 |
| 4,098,439 | 7/1978 | Blow, Jr. | 220/306 |
| 4,221,295 | 9/1980 | Tuchband et al. | 206/570 |
| 4,244,920 | 1/1981 | Manschot et al. | 220/306 |
| 4,284,200 | 8/1981 | Bush et al. | 220/306 |
| 4,434,907 | 3/1984 | Ingemann | 220/306 |
| 4,444,332 | 4/1984 | Widen et al. | 220/306 |
| 4,559,649 | 12/1985 | Burnett | 4/144.2 |
| 4,742,934 | 5/1988 | Michaud et al. | 220/306 |
| 4,834,261 | 5/1989 | Brdlik | 220/23.83 |
| 4,971,220 | 11/1990 | Kaufman et al. | 220/306 |
| 5,150,804 | 9/1992 | Blanchet et al. | 220/212 |
| 5,300,748 | 4/1994 | Colombo | 220/339 |

*Primary Examiner*—David T. Fidei
*Attorney, Agent, or Firm*—Welsh & Katz, Ltd.

[57] ABSTRACT

A sealable thermoformed container for containing liquids including a cup portion with an open end and a lid portion that is separable and sealably detachable from the cup. A cup sealing formation and lid formation are provided so that a liquid tight seal between the cup are formed when the lid is press-fit onto the top of the cup. Additionally, a detachable and disposable funnel may be attached to the cup for use in directing a stream of liquid into the cup prior to sealing.

13 Claims, 2 Drawing Sheets

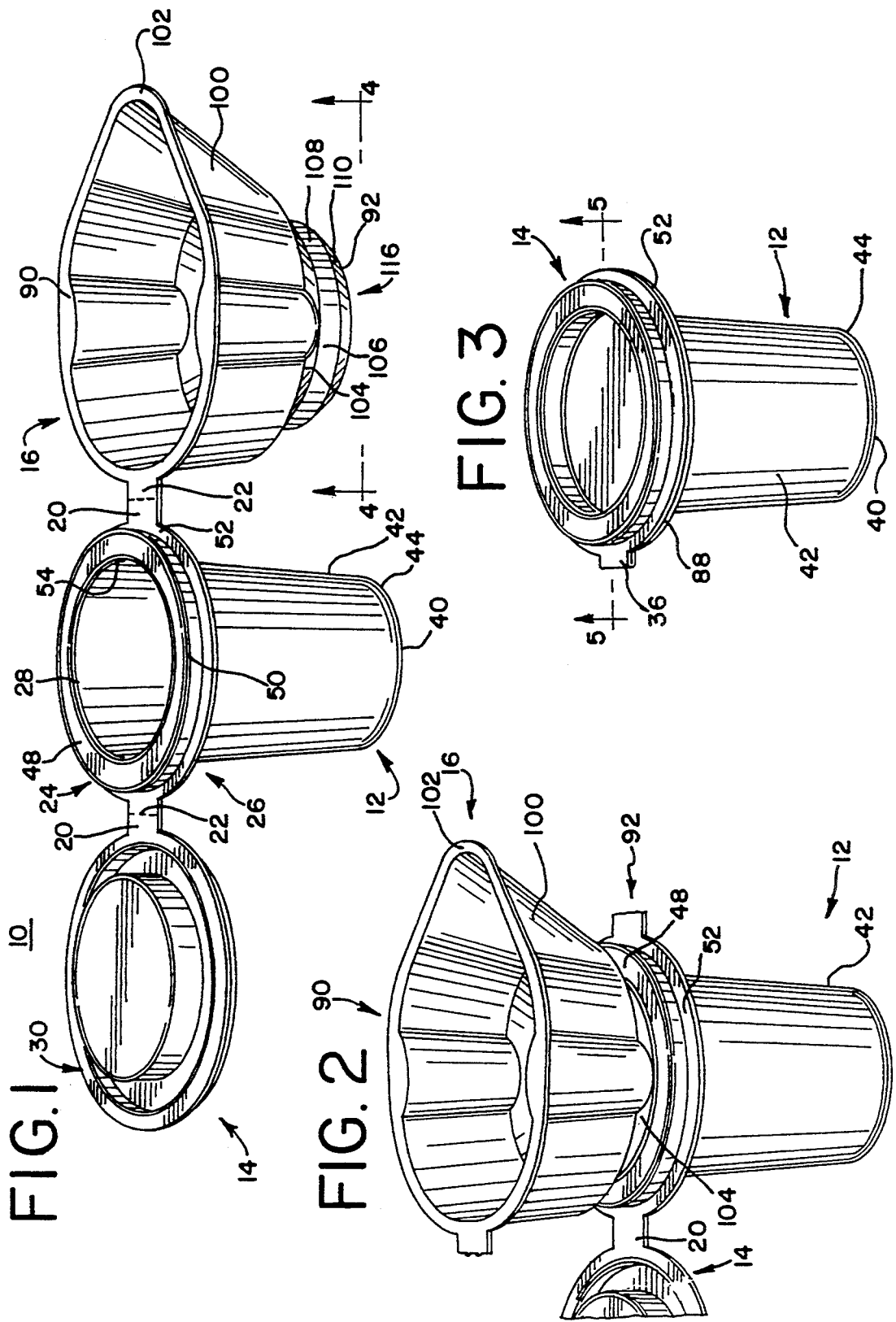

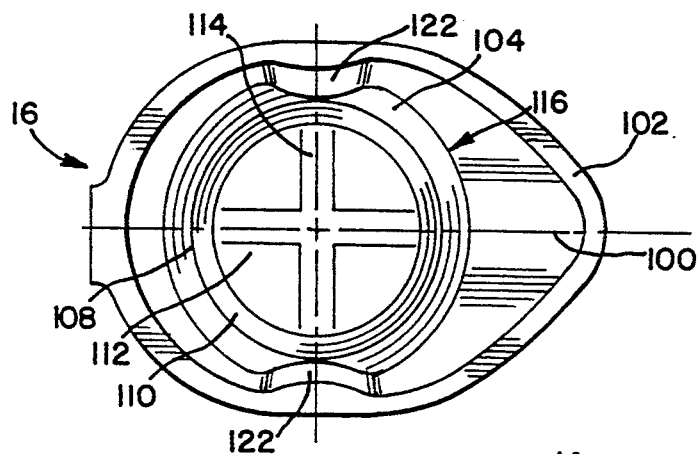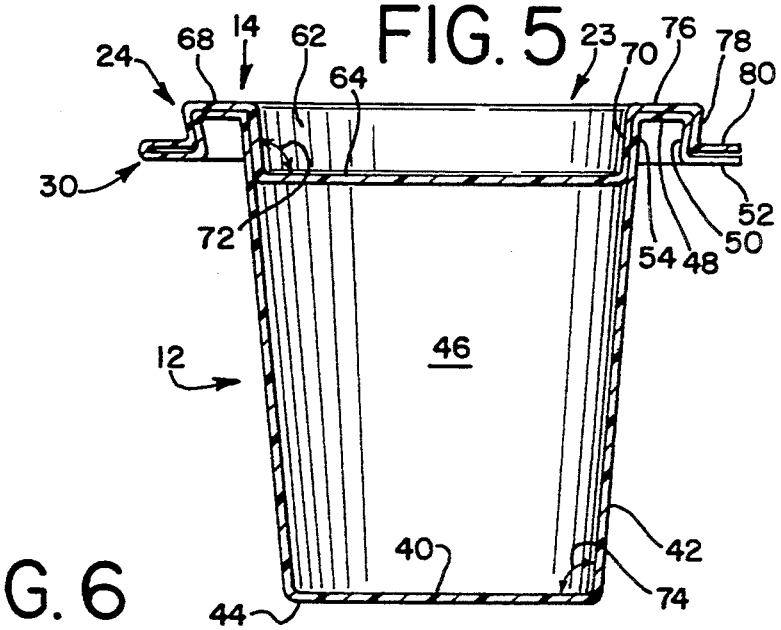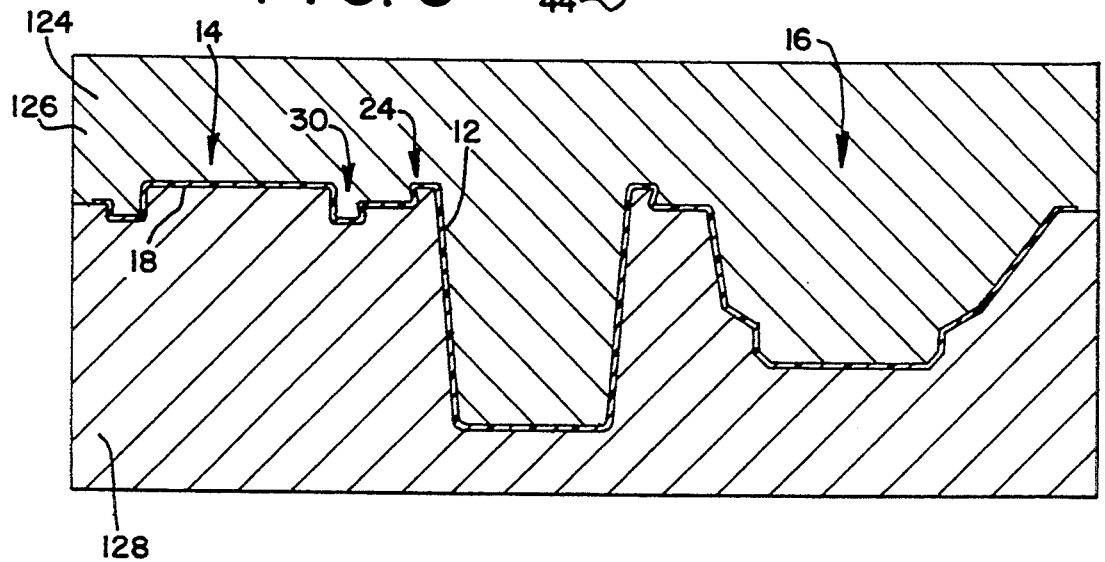

SEALABLE THERMOFORMED CONTAINER FOR LIQUIDS

BACKGROUND OF THE INVENTION

The present invention relates to a container for holding liquids, and more particularly to a disposable container for bodily fluid specimen, such container having a detachable lid and funnel so that liquid can easily and accurately be deposited in the container and then tightly sealed with the lid.

Currently, when samples of bodily fluids such as urine, need to be taken, a specimen is deposited into a small bottle or other container. Typically, these containers and their threaded caps are manufactured by relatively expensive injection molded process.

In typical medical facilities the patient deposits a specimen in a large intermediate container, then pours the contents of that container into the sample bottle and seals the sample bottle. However, this is wasteful, expensive, and inconvenient. Alternatively, the patient may be required to deposit the specimen directly into the small bottle. It is often difficult and cumbersome to deliver a stream of liquid into a small cup or bottle with accuracy. This process may be particularly cumbersome for young children, elderly persons, and female patients. Existing systems do not provide for a simple, efficient, and inexpensive way to direct a stream of bodily fluid or other liquid into a small cup or bottle. Not only are conventional methods for obtaining and depositing urine or other liquid samples cumbersome and expensive, but they are also potentially unsanitary due to the tendency to spill portions of the specimen during transfer from the intermediate container to the bottle.

Currently, specimen bottles or sample cups are produced and often distributed as separate pieces such as the cup or bottle and the associated cap or closure. Separate pieces are prone to being lost or misplaced.

Once the liquid specimen is in the container, the container must be sealed. Clearly, a tight seal between the bottle and the cap is required. This is typically accomplished by a washer or gasket contained within the cap and by threading the cap onto the bottle. When the cap is twisted onto the bottle, the sealing washer or gasket is compressed between the rim of the bottle and the cap to achieve a tight seal. Again, this requires an additional component and additional expense during manufacturing and assembly.

Other containers have eliminated the need for a sealing washer or gasket by requiring that the cap be applied to the bottle with sufficient force so that a tight seal is achieved without a washer or gasket. This is accomplished by twisting the cap onto the bottle or by pressing the cap onto the bottle with sufficient force. However, individuals with relatively weak hands and fingers, such as children and the elderly, may have difficulty exerting sufficient force necessary to obtain a positive seal.

It is therefore an object of the present invention to provide a sealable container for liquids that provides a liquid-tight seal between a cup and a lid.

another object of the present invention is to provide a sealable container for liquids that facilitate the direction of a stream of liquid into the cup.

A further object of the present invention is to provide a sealable container for liquids including a funnel that can be easily detached from the cup for use in directing a stream of liquid into the cup.

Yet another object of the present invention is to provide a sealable container for liquids where the funnel is self-aligning with the cup.

A still further object of the present invention is to provide a sealable container for liquids where all components, such as a cup portion, a lid portion and/or a funnel portion are formed from a single sheet of thermoformable material.

SUMMARY OF THE INVENTION

The disadvantages of the prior art liquid containers are overcome in accordance with the present invention by providing a sealable container for liquids including a cup portion with an open upper end and a lid portion that is separably attached to the cup. A cup sealing formation is disposed on the cup portion and a lid sealing formation is disposed on the lid portion are provided so that a leak-resistant seal between the cup portion and the lid portion is created when the lid portion is press-fit onto the cup portion.

More specifically, the present invention provides a sealable container that allows a stream of urine, other bodily fluids, or liquids to be easily and conveniently directed into the cup through the use of a detachable funnel. The cup, the lid, and the funnel are formed from a single sheet of thermoformable material where the funnel and the lid are attached to opposite sides of the cup by small bridge of connecting material. The lid and the funnel are easily detachable from the cup, however, the lid preferably remains attached to the cup so that it can be easily and conveniently folded over so that the lid contacts the open end of the cup forming a liquid-tight seal.

If the user of the container requires aid in directing a stream of liquid into the cup, the funnel may be detached from the cup and snugly inserted into the open end of the cup. Once the specimen has been deposited into the cup through the funnel, the funnel may be discarded. The funnel is preferably detached from the cup by gripping the funnel and tearing the bridge of connecting material along a pre-scored perforation line.

The cup, the lid, and the funnel are formed from a single sheet of thermoformable material and are formed from the same side of the material. All components are subject to identical heat conditions and deformation forces. Since all of the heat conditions and deformation forces are identical, the dimensions of each of the components are precise.

The dimensions of the sealing formation on the upper part of the cup are equal and complimentary to the dimensions of the sealing formation on the lid. The material used to produce the invention is a single sheet of thin gauge plastic. Because the dimensions on the cup sealing formation and the lid sealing formation are equal and both components are formed from thin gauge material, the lid sealing formation essentially "snaps" over the cup sealing formation creating an extremely tight seal. Additionally, due to the thinness of the material used, an extremely tight seal is achieved with a little pressure.

BRIEF DESCRIPTION OF THE DRAWINGS

FIG. 1 is a top prospective elevational view of the present sealable container for liquids depicting a cup, a lid, and a funnel;

FIG. 2 is a top prospective elevational view of the present sealable container for liquids depicting the funnel detached from the cup and mounted within the cup for directing a stream of liquid into the cup;

FIG. 3 is a top prospective elevational view of the sealable container for liquids depicting the cup with the lid sealing the cup;

FIG. 4 is a bottom elevational view taken along the line 4—4 of FIG. 1 and in the general direction indicated depicting the funnel and the funnel base having openings through which the liquid passes;

FIG. 5 is a side cross sectional view taken along the line 5—5 of FIG. 3 and in the direction generally indicated depicting the cup with the lid sealing the cup;

FIG. 6 is a vertical sectional view of the thermoforming mold apparatus in schematic form that is used to produce the sealable container for liquids depicting that the invention is formed from the same side of the thermoformable material.

DESCRIPTION OF THE PREFERRED EMBODIMENT

Referring now to the drawings, a sealable container for liquids is generally designated 10, and is preferably thermoformed from a single sheet of polymeric material selected for low cost, strength, durability, and recyclability. A preferred material is polyethylene glycol (PETG), however other plastics, including but not limited to styrene and acrylics may also be suitable.

Referring now to FIG. 1, the sealable container for liquids 10 includes a cup 12 for containing a specimen liquid, a lid 14 for releasably sealing the cup, and a funnel 16 or basin for directing a flow of liquid into the cup. In the preferred embodiment, the sealable container for liquids 10 is formed from a single sheet of polymeric material 18 (FIG. 6). Since the sealable container is formed from a single sheet of material 18 (FIG. 6), gripping tabs 20 are formed by a bridge material which connect the lid 14 and the funnel 16 to the cup 12. Preferable, the lid 14 and the funnel 16 are placed on opposite sides of the cup 12, however, alternate placement configurations are contemplated. A perforation 22 scored into each gripping tab 20 allows the lid 14 and the funnel 16 to be conveniently and easily detached from the cup 12 by grasping the gripping tab 20 in one hand and applying a sheering force to the funnel 16 or lid 14 respectively.

A cup sealing formation 24 disposed on a peripheral edge 26 of the open end 28 of the cup 12 is a structure that is complimentary in contour to a lid sealing formation 30 formed in the lid 14. Once a liquid specimen has been deposited into the cup 12, the lid 14 is folded over thus bending the gripping tab 20 into a generally "U" shaped 36 (FIG. 3) formation such that the lid sealing formation 30 engages the cup sealing formation 24 to form a liquid tight seal.

Referring now to FIG. 3, the lid 14 is shown sealing the cup 12 and any liquid contained therein. When the lid 14 is press-fit against the cup 12, a liquid tight seal 38 is formed between the two structures thus, any liquid within the cup is fully contained and will not leak.

Referring now to FIG. 5, the cup 12 and the lid 14 in the sealing position are generally shown. The cup 12 has a base 40 that is generally circular. However, the invention is not limited to this embodiment and other container shapes such as a rectangular container are also contemplated. A cylindrical cup side wall 42 projects from the periphery 44 of the base 40 to form a vessel 46 capable of containing a liquid. The cup side wall 42 is generally perpendicular to the base 40 but may have a substantial draft such that multiple thermoformed containers can be nested for convenient and efficient storage and shipping.

A top peripheral cup edge 48 disposed on the open end 28 of the cup 12 is integrally formed from the cup side wall. The top peripheral cup edge 48 projects radially from the cup side wall 42 and is generally parallel to the base 40 of the cup. A cup skirt 50 depends from the top peripheral cup edge 48 and is generally parallel to the cup side wall 42. However, the cup skirt 50 may be under cut to provide additional positive sealing characteristics. Additionally, the cup skirt 50 is integrally formed from the top peripheral cup edge 48. A cup flange 52 projects radially from the cup skirt 50 and is generally parallel to the top peripheral cup edge 48. The cup flange 52, the cup skirt 50, top peripheral cup edge 48, the cup side wall 42 and the base 40 are all integrally formed from a single sheet of material. The cup flange 52, the cup skirt 50, the top peripheral cup edge 48, and an upper portion 54 of the cup side wall 42 define the cup sealing formation 24.

The lid 14 is generally planar and circular in shape and is press-fit over the open end 28 of the cup 12 to seal the liquid contained within the cup. A circular recess 62 depends from a surface 68 of the lid 14 and is concentrical disposed on the lid. The circular recess 62 forms a recess base 64 parallel to the planar surface 68 of the lid 14 and a lid side wall 70 that is generally perpendicular to the planar surface of the base. However, an angle 72 formed between the lid side wall 70 and the recess base 64, if not perpendicular, will nonetheless be equal to an angle 74 formed between the cup base 40 and the cup side wall 42. This insures that when the lid 14 is press-fit onto the cup 12, the lid side wall 70 will be parallel to the cup side wall 42 thus, promoting a positive liquid seal. The surface 68 of the lid 14 includes a top peripheral lid edge 76 which projects radially from the lid side wall 70. skirt 78 depends from the top peripheral lid edge 76 and is generally parallel to the lid side wall 70. However, the lid skirt 78 may be undercut to provide additional positive sealing characteristics. A lid flange 80 projects radially from the lid skirt 78 and is generally parallel to the top peripheral lid edge 76. The lid flange 80, the lid skirt 78, the top peripheral lid edge 76, and the lid side wall 70 define the lid sealing formation 30. The lid sealing formation 38, and the lid 14 are formed from the single sheet of thermoformable material 18.

As shown in FIG. 5, the lid sealing formation 30 overlaps the cup sealing formation 24 when the lid 14 is pressed fit upon the cup 12. An advantage of the present invention is that an extremely tight seal is created between a lid sealing formation 30 and the cup sealing formation 24 because multiple surfaces of contact 84 are created. The lid flange 80 overlaps and contacts the cup flange 52, the lid skirt 78 overlaps and contacts the cup skirt 50, the top peripheral lid edge 76 overlaps and contacts the top peripheral cup edge 48, and the lid side wall 70 overlaps and contacts a portion 54 of the cup side wall 42. Thus, the multiple contact surfaces 84 create a positive seal between the lid sealing formation 30 and the cup sealing formation 24. Additionally, as previously mentioned, the cup skirt 50 and the lid skirt 78 are drafted to form an undercut. This creates a more positive structural interlock between the cup sealing formation 24 and the lid sealing formation 30.

Now referring to FIG. 6, the lid 14 and the cup 12 are formed from a same side 86 of the sheet of thermoformable material 18. Thus, when the invention is formed, all components are subject to identical heat and deformation forces. As such, the dimensions of the cup sealing formation 24 and the lid sealing formation 30 are equal within extremely precise tolerances. Such extremely tight tolerances create a very tight overlapping fit between the lid sealing formation 30 and the cup sealing formation 24 such that liquids can not penetrate the boundary 88 (FIG. 3) between the two formations.

Now referring back to FIGS. 1 and 2, the funnel 16 is generally shown. The funnel is formed attached to the cup 12 by the gripping tab 20 which is formed from a bridge of material between the cup and the funnel. As described earlier, the perforation 22 is scored into the gripping tab 20 to allow the funnel 16 to be easily removed from the cup 12 by gripping the gripping tab and applying a sheering force to the funnel.

The funnel 16 includes a wide end 90 and a narrow end 92 and is generally basin shaped. However, other funnel shapes are contemplated such as a substantial "V" shaped structure or any other structure capable of directing a stream of liquid into the cup 12. If the funnel 16 is required, the user detaches the funnel from the cup 12 and places the funnel over the open end 28 of the cup and exerts a slight amount of downward pressure so that a snug fit between the funnel and a cup is achieved. The user then directs a stream of liquid into the funnel 16 which then drains into the cup 12. The funnel 16 may then be discarded and the cup 12 is sealed with the lid 14.

The funnel 16 includes a funnel side wall 100 with a funnel lip 102 projecting radially from the funnel side wall and disposed at the wide end 90 of the funnel. The gripping tab 20 formed from the bridge of material between the cup 12 and the funnel 16 attaches to the funnel lip 102 and is the same plane as the funnel lip. A funnel shoulder 104 depends from the funnel side wall 100 and is disposed toward the narrow end 92 of the funnel. A funnel positioning wall 106 depends from the funnel shoulder 104 and forms a funnel skirt 108. A funnel taper 110 depends from the funnel skirt 108 and a planar funnel base 112 (FIG. 4) depends from the funnel taper and is parallel to the plane formed by the tunnel lip 102. The funnel lip 102, funnel side wall 100, funnel shoulder 104, funnel skirt, funnel taper 110, and funnel base 112 are integrally formed from the single sheet of thermoformable material 18.

The funnel taper 110 and the funnel skirt 108 form an alignment structure 116 that is used to easily and conveniently mount the funnel 16 on the cup 12. When the funnel 16 is placed over the cup 12, the slope of the funnel taper 110 causes the funnel to be aligned within the open end 28 of the cup 12. As downward pressure is exerted on the funnel 16, the funnel skirt 108 is concentrically engaged by the upper portion 54 of the cup side wall 42. Further downward pressure causes a greater degree of overlap between the funnel skirt 108 and the upper portion 54 of the cup side wall 42 until the funnel shoulder 104 engages and rests upon the top peripheral cup edge 48. At this point, the funnel 16 is snugly mounted on top of the cup 12. Once the liquid sample has been placed in the cup 12 through the funnel 16, the funnel may be removed at discarded.

Referring now to FIG. 4, the funnel 16 is shown removed from the cup 12. The planar base 112 of the funnel 16 is shown with material removed to form a plurality of openings 120. However, the invention is not limited to this configuration and other methods of providing openings within the funnel base 112 are contemplated such as a plurality of small holes or plurality of slots. In the present invention, a sufficient amount of material is removed or cut from the funnel base 112 to allow a stream of liquid to easily and quickly pass through the funnel 16 while sufficient base material remains to provide structure and strength to the funnel.

The funnel 16 includes two finger recesses 122 oppositely disposed on the funnel side wall 100 so that the user may conveniently grasp the funnel when inserting or removing the funnel from the cup 12. Additionally, the finger recesses 122 provide a convenient grasp point when directing the stream of liquid into the funnel.

Referring now to FIG. 6, the single sheet of thermoformable material 18 is shown from which the present invention is manufactured. As shown, the lid 14, the cup 12, and the funnel 16 are all formed from the single sheet of thermoformable material 18 and in addition, are formed from the same side 86 of the single sheet of thermoformable material. The sheet of thermoformable material 18 is sandwiched between two thermoformable dyes 124 such that the thermoformable material conforms to the exact contours of the thermoformable dye. All surfaces of the invention are subject to identical heat conditions and deformation forces during the manufacturing process. Since the heat conditions and deformation forces are uniform, all of the dimensions of the cup 12, the lid 14, and the funnel 16 are exact and within extremely small tolerances. Since the dimensions of the cup 12, the lid 16, and the funnel 16 are precise, the dimensions of the cup sealing formation 24 and the lid sealing formation 30 are similarly precise. This creates an extremely tight positive seal between the lid 14 and the cup 12 when the lid is press-fit over the cup.

While a particular embodiment of the sealable container for liquids has been shown and described, it will be appreciated by those skilled in the art that changes and modifications may be made thereto without departing from the invention in its broader aspects and as set forth in the following claims.

What is claimed is:

1. A sealable thermoformed container for containing liquids comprising:
   a cup portion adapted to contain liquid and having an open upper end;
   a lid portion;
   a cup sealing formation disposed on said cup and a lid sealing formation disposed on said lid for forming a releasably leak resistant seal between said cup portion and said lid portion when said cup portion and said lid portion are operatively coupled, said lid sealing formation including a substantially planar top peripheral lid edge circumscribing said open end of said cup, a recess base vertically displaced from the peripheral lid edge, an annular lid side wall joining said recess base to said peripheral lid edge, a lid skirt depending from said lid peripheral edge and being substantially parallel to said lid side wall, and a lid flange radially projecting from said lid skirt and being substantially parallel to said peripheral lid edge; and
   means for integrally attaching said cup portion to said lid portion to form a unitary container when said cup sealing formation and said lid sealing formation are completely uncoupled.

2. The container as defined in claim 1 further including a funnel integrally attached to one of said cup portion and said lid portion.

3. The container as defined in claim 1 wherein said cup further includes a generally planar base oppositely disposed from said open end of said cup;
a cup side wall projecting from the periphery of said base and defining a liquid retaining formation; and
said cup sealing formation disposed on a peripheral edge of said cup side wall and defining said open upper end.

4. The container as defined in claim 3 wherein said cup sealing formation further includes a top peripheral cup edge radially projecting from said cup side wall and being substantially parallel to said base, a cup skirt depending downward from said top peripheral cup edge; and
a cup flange radially projecting from said cup skirt and being substantially parallel to said top peripheral cup edge.

5. The container is defined in claim 1 wherein said lid sealing formation is configured to overlapping engage said cup sealing formation such that said lid side wall frictionally engages an inner face of a cup side wall, said peripheral lid edge overlappingly engages a top peripheral cup edge, said lid skirt overlappingly engages a cup skirt, and said lid flange overlappingly engages a cup flange, to form a releasable leak-resistant seal.

6. The container assembly as defined in claim 2 wherein said funnel and said lid portion are secured to said cup portion to be sequentially detachable from said cup portion.

7. The container assembly as defined in claim 2 wherein said funnel has a lower end dimensioned to be inserted into said open end of said cup portion and defining at least one opening.

8. The container assembly as defined in claim 1 wherein said cup portion further includes a generally planar base oppositely disposed from said open end of said cup portion;
a cup side wall projecting from said base and defining a liquid retaining formation;
a cup sealing formation disposed on a peripheral edge of said cup side wall and defining said open upper end.

9. The container assembly as defined in claim 8 wherein said cup sealing formation further includes a top peripheral cup edge radially projecting from said cup side wall and being substantially parallel to said base;
a cup skirt depending from said top peripheral cup edge and being substantially parallel to said cup side wall; and
a cup flange radially projecting from said cup skirt and being substantially parallel to said top peripheral cup edge.

10. The container assembly as defined in claim 2 wherein said funnel includes a base configured to define at least one opening for allowing a liquid to pass there through.

11. The thermoformed container as defined in claim 2 wherein said funnel further includes a funnel side wall;
a funnel lip radially projecting from said funnel side wall and disposed on said wide end of said funnel;
a funnel shoulder depending from said side wall and oppositely disposed from said lip;
a funnel positioning wall depending from said shoulder forming a funnel skirt;
a funnel taper depending from said funnel skirt; and
a funnel base depending from said funnel taper.

12. The container assembly as defined in claim 2 wherein a narrow end of said funnel is configured to aligningly position said funnel within said open end of said cup portion such that a funnel positioning wall coaxially engages a portion of a cup side wall and are funnel shoulder engages a top peripheral cup edge for releasably attaching said funnel to said cup portion.

13. The container assembly as defined in claim 2 further including tab means for connecting said lid portion and said funnel to said cup portion to facilitate handling.

* * * * *